United States Patent
Davis

(10) Patent No.: US 6,927,319 B2
(45) Date of Patent: Aug. 9, 2005

(54) NATURAL HERBICIDE RESISTANCE IN SOYBEANS

(75) Inventor: William H. Davis, Plainview, TX (US)

(73) Assignee: Natural Genes, Inc., Plainview, TX (US)

( * ) Notice: Subject to any disclaimer, the term of this patent is extended or adjusted under 35 U.S.C. 154(b) by 231 days.

(21) Appl. No.: 10/119,194

(22) Filed: Apr. 10, 2002

(65) Prior Publication Data

US 2003/0196226 A1 Oct. 16, 2003

(51) Int. Cl.$^7$ .................. A01H 1/00; A01H 1/04; C12Q 1/68
(52) U.S. Cl. ............................ 800/266; 435/6
(58) Field of Search .................. 435/6; 800/276, 800/266, 270, 300, 312

(56) References Cited

U.S. PATENT DOCUMENTS

| | | | |
|---|---|---|---|
| 4,971,908 A | 11/1990 | Kishore et al. | 536/23.2 |
| 5,145,783 A | 9/1992 | Kishore et al. | 800/300 |
| 5,312,910 A | 5/1994 | Kishore et al. | 536/23.2 |
| 5,352,605 A | 10/1994 | Fraley et al. | 435/418 |
| 5,530,196 A | 6/1996 | Fraley et al. | 800/298 |
| 5,858,742 A | 1/1999 | Fraley et al. | 435/468 |

OTHER PUBLICATIONS

Sebastian et al 1987 Crop Science vol. 27, pp. 948–952.*
Hwang et al 2000 Journal of Biochemistry and Molecular Biology vol. 33, No. 6, pp. 537–546.*
Developing Plant Varieties Resistant to Sulfonylurea Herbicides, R.S. Chaleff, et al., Department of Central Research and Development, Experimental Station, E.I. DuPont and Company, Wilmington, Delaware 19898, Molecular Strategies for Crop Protection, pp. 415 to 425, 1987, Alan R. Liss, Inc.

Semidominant Soybean Mutation for Resistance to Sulfonylurea Herbicides, S.A. Sebastian, et al., Published in Crop Sci. 29: pp. 1403 to 1408. (1989).

Soybean Mutants with Increased Tolerance for Sulfonylurea Herbicides, Scott A. Sebastian, et al., Published in Crop Sci. 27: pp. 948 to 952. (1987).

* cited by examiner

*Primary Examiner*—David H Kruse
(74) *Attorney, Agent, or Firm*—Burns, Doane, Swecker & Mathis, LLP

(57) ABSTRACT

A process is provided for detecting and isolating soybean plants in the absence of induced mutagenesis that exhibit naturally-occurring genetically-controlled glyphosate herbicide resistance that is not attributable to genetic engineering. Mature soybean seeds initially are soaked in a liquid comprising a glyphosate herbicide for a period of time sufficient for the herbicide to reach the embryos of the soybean seeds. Following such soaking the soybean seeds are planted to produce at least one soybean plant or a descendant thereof in a subsequent generation that displays resistance to glyphosate herbicide. The existence of the naturally-occurring glyphosate herbicide resistance in a soybean plant is confirmed by demonstrating the absence of a foreign gene for herbicide resistance that has been introduced by genetic engineering. Such herbicide resistance is generally-controlled and can be reliably expressed and transferred to other soybean plants by conventional plant breeding methods.

15 Claims, No Drawings

NATURAL HERBICIDE RESISTANCE IN SOYBEANS

FIELD OF THE INVENTION

The invention provides a process for selecting soybean plants and generating soybean lines that exhibit naturally-occurring genetically-controlled herbicide resistance in the absence of genetic engineering, soybean lines that exhibit naturally-occurring herbicide resistance, the naturally-occurring genes that confer such herbicide resistance that are exposed by the aforementioned selection process, and the use of such herbicide resistance genes through genetic engineering to confer herbicide resistance to other plants that are naturally sensitive to herbicide exposure.

BACKGROUND OF THE INVENTION

Soybean plants of the genus *Glycine max* L. have long been recognized to be an important crop, which is being grown in many parts of the world. This crop is grown primarily for the seeds that are produced. These seeds may be used for planting or as a source of edible and industrial oils with the residue serving as a livestock feed supplement.

Modern agriculture practices are increasingly taking advantage of herbicides to eliminate unwanted weeds from soybean fields and to minimize the expense of tilling fields to remove unwanted weeds. Presently, there are no herbicides that kill on contact (post-emergent herbicides) that can be used with conventional soybean plants without causing excessive crop injury. The herbicide glyphosate is an effective non-selective post-emergent herbicide. Plant transformation/genetic engineering has been used in the past to modify soybean plants to incorporate resistance to the herbicidal effects of glyphosate.

Genetic engineering/plant transformation involves the incorporation of a gene for herbicide resistance into the chromosome of the soybean plant. Such procedures require special expertise and can be very costly. The "resistance" gene is part of a construct that is placed in the plant to impart herbicide resistance. In addition, the construct contains promoters that are responsible for activating the gene in select portions or in all parts of the plant. The presence or absence of these promoters is used to determine if the plant is the result of genetic engineering/plant transformation. The gene construct that is in commercially available in soybean plants includes the promoters, CaMV35S, and NOS marker gene. Representative prior publications that concern the use of genetic engineering to produce such herbicide resistance include U.S. Pat. Nos. 4,971,908; 5,145,783; 5,312,910; 5,352,605; 5,530,196; and 5,858,742.

It also has been proposed in the past to attempt to create some sulfonylurea herbicide resistance in soybean plants through the use of induced mutagensis. See, for instance, (a) "Molecular Strategies for Crop Protection", by R. S. Chaleff et al., Pages 415 to 425 (1987), (b) "Soybean Mutants with Increased Tolerance for Sulfonylurea Herbicides", by Scott A. Sebastian et al. *Crop Science,* 27, Pages 948 to 952 (1987), and (c) "Semidominant Soybean Mutation for Resistance to Sulfonylurea Herbicides", S. A. Sebastian et al., *Crop Science,* 29, Pages 1403 to 1408 (1989). The resulting plants display no glyphosate herbicide resistance, often display limited resistant to sulfonylurea herbicide, and such herbicide is sometimes ineffective to kill weeds in view of acquired resistance to the sulfonylurea herbicide.

The objective of the present invention is to provide a new and reliable route for providing genetically-controlled herbicide resistance in soybean plants in the absence of induced mutagensis or the insertion of a foreign gene. A further objective of the present invention is to provide a soybean plant having genetically-controlled resistance that can be contacted with the herbicide in all stages of the life cycle of the plant and seeds capable of producing the same. The invention also provides a soybean plant that contains within its genome a naturally occurring genetic determinant that confers herbicide resistance that can be genetically mapped and physically isolated for use in breeding or biotechnological programs. Such genetic determinants represent novel genetic mechanisms for conferring herbicide resistance to host plants.

These and other objectives, as well as the scope, nature and utilization of the claimed invention will be apparent to those skilled in this area of technology from the following detailed description and appended claims.

SUMMARY OF THE INVENTION

The invention provides a method for detecting, isolating, and developing soybean plants that exhibit naturally-occurring genetically-controlled herbicide resistance in the absence of genetic engineering/plant transformation. The method comprises soaking mature soybean seeds in a liquid comprising a herbicide for a period of time sufficient for the herbicide to reach the embryos of the soybean seeds, planting said soybean seeds following said soaking in a growing medium and producing at least one soybean plant that displays resistance to the herbicide, selecting a soybean plant which exhibits genetically-controlled herbicide resistance that is not attributable to a foreign gene for herbicide resistance introduced by genetic engineering and is the result of the action of a naturally-occurring herbicide resistance gene. In a preferred embodiment the herbicide is glyphosate.

The invention also provides a method for selecting individual soybean plants that are herbicide resistant from soybean germplasm or soybean lines identified as described in the method identified above. This method entails planting large numbers of seeds from soybean germplasm or soybean lines identified using the method described above, spraying plants with liquid herbicide solutions at herbicide concentrations sufficient to kill soybean plants and weeds, selecting survivors from the herbicide treatments and selecting soybean plants which exhibit naturally-occurring genetically-controlled herbicide resistance that is not attributable to a foreign gene for herbicide resistance introduced by genetic engineering from the survivors.

The invention also provides the isolation of seeds from the individual herbicide resistant soybean plants identified using the method described above.

The invention also provides the establishment of plants derived from the seeds described above.

The invention also provides the isolation of the nucleic acids that direct natural herbicide resistance from the genome of the soybean plants isolated using the methods described herein.

The invention also provides DNA constructs comprising the nucleic acids as described. In such constructs the nucleic acid is operatively linked to plant gene expression control sequences.

The invention also provides vectors comprising the DNA construct as described herein.

The invention further provides a transgenic plant or part of a plant. The transgenic plant or part of a plant comprises the nucleic acid operatively linked to plant gene expression control sequences produced according to the present invention.

The invention also provides a method of controlling weeds in a field containing herbicide resistant soybean plants of the present invention or transgenic plants utilizing nucleic acid sequences, constructs or vectors formed in accordance with the present invention.

The invention further provides the following:

A soybean plant or seed of the line NatGen 1 or its descendants having genetically-controlled glyphosate herbicide resistance that is attributable to the homozygous gene $NG^{R1}NG^{R1}$ obtainable from ATCC Accession No. PITA-4774.

A soybean plant or seed of the line NatGen 2 or its descendants having genetically-controlled herbicide resistance that is attributable to the homozygous gene $NG^{R2}NG^{R2}$.

A soybean plant or seed of the line NatGen 3 or its descendants having genetically-controlled herbicide resistance that is attributable to the homozygous gene $NG^{R3}NG^{R3}$ obtainable from ATCC Accession No. PTA-5937.

A soybean plant or seed of the line NatGen 4 or its descendants having genetically-controlled herbicide resistance that is attributable to the homozygous gene $NG^{R4}NG^{R4}$.

A soybean plant or seed of the line NatGen 5 or its descendants having genetically-controlled herbicide resistance that is attributable to the homozygous gene $NG^{R5}NG^{R5}$.

A soybean plant or seed of the line NatGen 6 or its descendants having genetically-controlled herbicide resistance that is attributable to the homozygous gene $NG^{R6}NG^{R6}$.

Isolated nucleic acids comprising of any of the $NG^{R1-R6}NG^{R1-R6}$ genes, or gene systems, and expression controlling elements derived from soybean plants are made possible which when expressed in a soybean plants, other dicotyledonous crops, or monocotyledonous crops (after suitable modification to the coding sequence and/or controlling elements that are standard expedients to one skilled in art) render that plant and its progeny resistant to the herbicide.

DESCRIPTION OF PREFERRED EMBODIMENTS

Presently useful herbicide resistance in commercial soybean varieties is limited to only a few herbicides, the most important one being glyphosate. Resistance to glyphosate has been achieved by the introduction of bacterial genes into soybean germplasm that either codes for target enzymes that are not affected by the herbicide or for enzymes that break down the herbicide into an inactive form. Such genes have been constructed and introduced into soybean plants using standard genetic engineering techniques of gene construction and plant transformation. Examples of such genes are described in U.S. Pat. Nos. 4,971,908; 5,145,783; 5,312,910; 5,352,605; 5,530,196; and 5,858,742. These genes are engineered to function in a plant cell and are placed under the control of a promoter element, commonly derived from a plant viral genome that allows for the constitutive expression of the herbicide resistant or degradative enzyme. Such biotechnological strategies demand a lengthy and expensive research and development program. The present invention provides a method by which naturally-occurring genes that confer herbicide resistance and that are already present in soybean germplasm stocks can be revealed, identified and exploited for commercial use in both conventional and biotechnological breeding programs.

The initial step of the process of the present invention soybean seeds are soaked in a liquid comprising a herbicide. Commonly the herbicide is present in concentrations that are sufficient to kill conventional soybean plants as well as weeds that commonly occur in soybean fields. Representative herbicides are glyphosate, 2,4-dichlorophenoxyacetic acid, glufosinate ammonium butanoic acid, 3,5-dibromo-4-hydroxybenzonitrile, etc. In a preferred embodiment the herbicide is a glyphosate and the herbicide concentration is sufficient to kill soybean plants at the commercially used rate of 1 quart per acre of a glyphosate preparation that is 41% active ingredient (N-(phosphonomethyl) glycine. Such herbicide is N-(phosphonomethyl)glycine of the chemical formula;

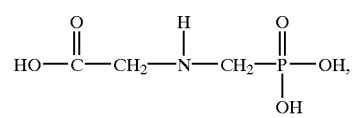

and is commercially available from Monsanto Corporation under the ROUNDUP trademark as well as from other companies under various trademarks. This herbicide is a non-selective, broad spectrum, post-emergence herbicide that is registered for use in more than fifty crops. This molecule is an acid, which dissociates in aqueous solution to form phytoxic anions. Several anionic forms are known. As used herein, the name "glyphosate" refers to the acid and its anions. Glyphosate inhibits the shikimic acid pathway that provides a precursor for the synthesis of aromatic amino acids. Specifically, glyphosate curbs the conversion of phosphoenolpyruvate and 3-phosphoshikimic acid to 5-enolpyruvyl-3-phospho shikimic acid by inhibiting the enzyme 5-enolpyruvyl-3phosphoshikimiate synthase. Although glyphosate is identified in this preferred embodiment, other herbicides, such as 2,4-dichlorophenoxyacetic acid, glufosinate ammonium butanoic acid, or 3,5-dibromo-4-hydroxybenzonitrile, etc., can be used to identify and isolate herbicide resistance genes present in the soybean germplasm.

Preferably the soybean seeds are soaked in an aqueous solution of the herbicide. Commonly the herbicide is present in the solution in a concentration of approximately 2 to 6 percent by weight, and most preferably in a concentration of approximately 2.5 percent by weight. These concentrations have been found to be effective for the herbicide glyphosate. Concentrations for treatments with other herbicides can be determined empirically. Commonly the soybean seeds are simply immersed or suspended in the liquid comprising the herbicide. The soaking of soybean seeds is conducted for a period of time that is at least sufficient for the herbicide to reach the embryos of the soybean seeds. A soaking time of at least 6 hours has been found to yield good results. The liquid comprising the herbicide can be simply provided at room temperature when the soybean seeds are in contact with the liquid and are undergoing such soaking.

Following soaking in the herbicide, the resultant seeds are planted in a growing medium (e.g., soil) and germination of the seeds is attempted to produce soybean plants that display herbicide resistance. The herbicide resistance can be confirmed by spraying the resulting soybean plants with the same herbicide in a concentration typically used to kill weeds growing in a soybean field.

Alternatively, such screening of the resulting soybean plants for herbicide resistance can include the inclusion of the herbicide in the growing medium where the resulting seeds are planted. Good results are obtained in a preferred embodiment when one gallon of a solution containing the herbicide in a concentration of approximately 2 to 6 percent by weight is added to each 4 gallons of soil. The presence of the herbicide in the soil helps to assure that an atypical soybean seed having a harder seed coat is effectively exposed to the herbicide. It has been found that a small proportion of the seeds following soaking in a liquid comprising a herbicide, and planting in a growth medium, will germinate and yield soybean plants that exhibit resistance to the herbicide.

The percentage of the soybean plants that will grow normally following such seed treatments has been found to vary from variety to variety. Some varieties have produced no surviving plants in tests to date. Some varieties have produced up to approximately 1 surviving plant per 1,000 seeds, and others approximately 1 surviving plant per 25,000 seeds. The herbicide resistance of the resulting plants can be further confirmed by another contact (e.g., by spraying) with the herbicide. A simple field test kit for herbicide resistance is available from AIT Company of Iroquois, S. Dak., as well as from other sources.

A portion of a herbicide-resistant soybean plant produced following such germination or a descendant thereof is analyzed to confirm that the manifest herbicide resistance is not the result of genetic engineering involving the insertion by man of a foreign gene that is not naturally-occurring into the soybean plant. This preferably is done by checking for the presence of a promoter or genetic marker sequences that were introduced by man when inserting a foreign gene construct for herbicide resistance into the soybean germplasm. This analysis is used to confirm that the subject soybean plant is not a genetically-modified organism and that the manifest herbicide resistance is attributable to a naturally-occurring genetic basis other than that introduced by genetic engineering. More specifically, this analysis is used to confirm that the resulting herbicide-resistant soybean plant or plants were not derived in some manner (e.g., by outcrossing) from a soybean plant that has been genetically engineered for herbicide resistance.

In accordance with the process of the present invention a soybean plant is next selected in which the herbicide resistance is under genetic control and in which there is no evidence of the use of genetic engineering to produce the herbicide resistance, such as the presence of a chimeric plant promoter-bacterial gene construct for such herbicide resistance. Any suitable technique can be utilized to confirm the absence of the use of genetic engineering to produce the herbicide resistance. For instance, a DNA-polymerase chain reaction can be utilized. In a preferred embodiment, a DNA-polymerase chain reaction is carried out on a portion of a soybean plant leaf. This analysis can be carried out to advantage when analyzing a portion of a young growing leaf. A DNA sequence analysis can be utilized to confirm that the gene for herbicide resistance does not conform to the sequence of a foreign gene inserted into the soybean genome by genetic engineering. At this time the DNA sequences that are relevant are those that are in common use in commercially-grown transgenic crops. The sequences that are in use and are detectable by PCR screening are the sequences for the cauliflower mosaic viral 35S promoter, the figwort mosaic virus (FMV) promoter, the individual coding sequences that encode proteins that when expressed render the plant resistant to a particular herbicide, e.g., the 5-enolpyruvylshikimate-3-phosphate synthase (EPSPS) gene from petunia enabling tolerance to glyphosate, and the chimeric NOS-NPTII-NOS gene for kanamycin resistance.

The presence and expression of the petunia EPSPS gene conferring glyphosate resistance can also be detected by use of a specific antibody directed against the protein encoded by this gene. The CP4 gene for glyphosate herbicide resistance when present also can be detected.

Also, contemplated by the instant invention are the nucleic acids which comprise the genes which when expressed in the soybean plant provide herbicide resistance to that plant. Once a soybean plant which exhibits genetically-controlled herbicide resistance that is not attributable to genetic engineering has been identified, the gene responsible for the naturally-occurring herbicide resistance can be genetically mapped, identified, isolated, and sequenced by anyone competent in the art. See, *Plant Genomes: Methods for genetic and physical mapping*. J. S. Beckmann and T. C. Osborn, 1992, Kluwer Academic Publishers, *Genome mapping in Plants*. A. Paterson, 1996 Harcourt Brace and Co, *Maize Genome mapping* A. Kalinski 1996, Diane Publishing Co., and *Methods in Molecular Biology Vol. 82: Arabidopsis Protocols* J. M. Martinez-Zapater and J. Salinas, 1998 Humana Press. The isolated nucleic acid encoding the gene conferring the naturally-occurring herbicide resistance encodes a protein responsible for causing the plant to be herbicide resistant. This isolated nucleic acid can then be used to (1) identify other nucleic acids which may contain naturally-occurring mutations that provide herbicide resistance to soybean plants; (2) introduce the isolated nucleic acid into a soybean plant which lacks herbicide resistance by genetic engineering techniques which are known to an artisan of ordinary skill; (3) insert the isolated nucleic acid into a suitable vector which can be expressed in a soybean plant; and (4) insert the vector into a plant cell (e.g., a soybean plant cell).

The present invention also contemplates the fabrication of DNA constructs comprising the isolated nucleic acid sequence containing the coding sequence from the gene that confers herbicide resistance operatively linked to plant gene expression control sequences. "DNA constructs" are defined herein to be constructed (not-naturally occurring) DNA molecules useful for introducing DNA into host cells, and the term includes chimeric genes, expression cassettes, and vectors.

As used herein "operatively linked" refers to the linking of DNA sequences (including the order of the sequences, the orientation of the sequences, and the relative spacing of the various sequences) in such a manner that the encoded protein is expressed. Methods of operatively linking expression control sequences to coding sequences are well known in the art. See, e.g., Maniatis et al., *Molecular cloning: A Laboratory Manual*. Cold Spring Harbor, N.Y. (1982), Sambrook et al., *Molecular Cloning: A Laboratory Manual*, Cold Spring Harbor, N.Y. (1989).

"Expression control sequences" are DNA sequences involved in any way in the control of transcription or translation. Suitable expression control sequences and methods of making and using them are known in the art.

The expression control sequences must include a promoter. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds, *Nucleic Acids Res.*, 15, 2343–61 (1987). Also, the location of the promoter relative to the transcription start may be optimized. See, e.g, Roberts et al., Proc. *Natl. Acad. Sci. USA*, 76, 760–4 (1979). Many suitable promoters for use in plants are well known in the art.

For instance, suitable constitutive promoters for use in plants include: the promoters of plant viruses, such as the peanut chlorotic streak *caulimovirus* (PCISV) promoter (U.S. Pat. No. 5,850,019), the 35S and 19S promoter from cauliflower mosaic virus (CaMV) (Odell et al., 1 313:3810–812, 1985), promoters of the *Chlorella* virus methyltransferase genes (U.S. Pat. No. 5,563,328), and the full-length transcript promoter from figwort mosaic virus (FMV) (U.S. Pat. No. 5,378,619); the promoters from such genes as rice actin (McElroy et al., *Plant Cell* 2:163–171 (1990)), ubiquitin (Christiansen et al., *Plant Mol. Biol.* 12:619–632 (1989)), and (Christiansen et al., *Plant Mol. Biol.* 18: 675–689 (1992)), pEMU (Last et al., *Theor. Appl Genet.* 81:581–588 (1991)), MAS (Velten et al., *Embo J.* 3:2723–2730 (1984)), maize H# histone (Lepetit et al., *Mol. Gen. Genet.* 231:276–285 (1992) and Atanassova et al., *Plant Journal* 2:291–300 (1992)), *Brassica napus* ALS3 (International Publication No. WO 97/41228); and promoters of various *Agrobacterium* genes (See U.S. Pat. Nos. 4,771,002; 5,102,796; 5,182,200; and 5,428,147).

Suitable inducible promoters for use in plants include: the promoter from the ACE1 system which responds to copper (Mett et al., PNAS 90:4567–4571 (1993)): the promoter of the maize In2 gene which responds to benzenesulfonomide herbicide safeners (U.S. Pat. No. 5,364,780 and Gatz et al *Mol. Gen. Genet.* 243:32–38 (1994)), and the promoter of the Tet repressor from Tn10 (Gatz et al *Mol. Gen. Genet.* 227:229–237 (1991)). A particularly preferred promoter for use in plants is one that responds to an inducing agent to which plants normally do not respond. An exemplary inducible promoter of this type is the inducible promoter from a steroid hormone gene, the transcriptional activity of which is induced by a glucosteroid hormone (Schena et al., PNAS 88:10421 (1991)) or the recent application of a chimeric transcription activator, XVE, for use in an estrogen receptor-based inducible plant expression system activated by estradiol (Zou et al., *The Plant Journal* 24 265–273 (2000)). Other inducible promoters for use in plants are described in European Application No. 332104, and International Publication Nos. WO 93/21334 and WO 97/06269.

Finally, promoters composed of portions of other promoters and partially or totally synthetic promoters can be used. See, e.g., Ni et al., *Plant Journal* 7:661–676 (1995) and International Publication No. WO 95/14098 describing such promoters for use in plants.

The promoter may include, or be modified to include, one or more enhancer elements. Preferably, the promoter will include a plurality of enhancer elements. Promoters containing enhancer elements provide for higher levels of transcription as compared to promoters that do not include them. Suitable enhancer elements for use in plants include the PCISV enhancer element (U.S. Pat. No. 5,850,019), the CaMV35S enhancer element (U.S. Pat. Nos. 5,106,739 and 5,164,316) and the FMV enhancer element (Maiti et al., *Transgenic Research* 6:143–156 (1997)). See also, International Publication No. WO 96/23898 and *Enhancers and Eukaryotic Expression* (Cold Spring Harbor Press, Cold Spring Harbor, N.Y., 1983).

For efficient expression, the coding sequences are preferably also operatively linked to a 3' untranslated sequence. The 3' untranslated sequence will include a transcription termination sequence and a polyadenylation sequence. The 3' untranslated region can be obtained from the flanking regions of genes from *Agrobacterium*, plant viruses, plants and other eukaryotes. Suitable 3' untranslated sequences for use in plants include those of the cauliflower mosaic virus 35S gene, the phaseolin seed storage protein gene, the pea ribulose-1,5-bisphosphate carboxylase small subunit E9 gene, the soybean 7S storage protein gene, the octopine synthase gene, and the nopaline synthase gene.

A 5' untranslated leader sequence is also employed. The 5' untranslated leader sequence is the portion of an mRNA which extends from the 5'CAP site to the translation initiation codon. This region of the mRNA is necessary for translation initiation in plants and plays a role in the regulation of gene expression. Suitable 5' untranslated leader sequence for use in plants includes those of alfalfa mosaic virus, cucumber mosaic virus coat protein gene, and tobacco mosaic virus.

The DNA construct may be a vector. The vector may contain one or more replication systems which allow it to replicate in host cells. Self-replicating vectors include plasmids, cosmids and virus vectors. Alternatively, the vector may be an integrating vector which allows the integration into the host cell's chromosome of the DNA sequence encoding the herbicide resistance gene product. The vector desirably also has unique restriction sites for the insertion of DNA sequences. If a vector does not have unique restriction sites it may be modified to introduce or eliminate restriction sites, to make it more suitable for further manipulation.

Vectors suitable for use in expressing the nucleic acids, which when expressed in a plant confer herbicide resistance, include but are not limited to pMON979, pMON977, pMON886, pCaMVCN, and vectors derived from the tumor inducing (Ti) plasmid of *Agrobacterium tumefaciens* described by Rogers et al., Meth. Enz~mol. 153:253–77 (1987). The nucleic acid is inserted into the vector such that it is operably linked to a suitable plant active promoter. Suitable plant active promoters for use with the nucleic acids include CaMV35S, ACTIN, NOS and PCSLV promoters. The vectors comprising the nucleic acid can be inserted into a plant cell using a variety of known methods. For example, DNA transformation of plant cells include but are not limited to *Agrobacterium*-mediated plant transformation, protoplast transformation, gene transfer into pollen, and injection into reproductive organs, injection into immature embryos and particle bombardment. These methods are described more fully in U.S. Pat. No. 5,756,290 and the references cited therein. Site-specific recombination systems can also be employed to reduce the copy number and random integration of the nucleic acid into the soybean plant genome. For example, the Cre/lox system can be used to immediate lox site-specific recombination in plant cells. This method can be found in Choi et al., *Nuc. Acids Res.* 28: B19 (2000) and elsewhere.

The herbicide resistance that results from the present invention is shown to be an infrequent naturally-occurring dominant genetic mutant and not the product of an introduced genetic modification or a mutation induced by man. The process steps of the of the present invention have been found to enable the isolation of such naturally-occurring genetic mutants in soybean plants on a reliable basis. Such herbicide resistance is under genetic control through the expression of one or more dominant gene pairs for herbicide resistance and can be readily transferred to other soybean varieties and lines, through the use of conventional plant breeding. Hereafter such dominant gene pairs have been designated as $NG^{Rn}$, where "n" can be any number (in this specification $NG^{R1}$ through $NG^{R6}$ have been utilized).

The herbicide resistance of the present invention can be provided in true-breeding soybean varieties and lines as well as in $F_1$ soybean hybrids. When forming $F_1$ hybrids, the requisite genetic control is provided in both parent plants (e.g., in cytoplasmic male sterile and restorer parent plants).

Also, soybean plants can be provided that are resistant to more than one herbicide when appropriate naturally-occurring genes are incorporated into a single soybean plant such as by the use of conventional plant breeding followed by selection. The techniques used in such a plant breeding program are commonly known to those skilled in the art and are described, in part, in the treatise "Breeding Field Crops" 1995 4th Edition by J. Poehlman and D. Sleper, published by Iowa State University Press, Ames, Iowa.

Herbicide resistant soybean plants of the present invention can be sprayed with herbicide at any stage of the plant life cycle without deleterious results. For instance, herbicide resistant soybean plants of the present invention can be treated with a herbicide from the seed stage through flowering and during pod formation and filling without injury. This is not always possible with genetically engineered herbicide resistance. A longer and safer period for spraying with a herbicide is provided by this invention. Accordingly, a soybean grower when utilizing soybean plants of the present invention, can spray the soybean field with herbicide whenever the need for weed control is apparent without restriction with respect to timing. This provides greater weed control options and more flexibility to the soybean grower.

In yet another embodiment, the invention provides a method of controlling weeds in a field where herbicide resistant soybean plants of the present invention or transgenic plants utilizing nucleic acid sequences, constructs or vectors in accordance the present invention are growing. The method comprises applying an effective amount of herbicide, in the preferred embodiment a glyphosate herbicide, to the field to control the weeds. Methods of applying herbicides, including glyphosate, and the herbicide concentrations that are effective to control various types of weeds are known. See, *Crop Protection Reference* (Chemical and Pharmaceutical Press, Inc., New York, N.Y., 11th edition 1995).

The following Examples are presented as specific illustrations of the claimed invention. It should be understood, however, that the invention is not limited to the specific details of the Examples.

EXAMPLES

In the following examples preferred embodiments are provided for the selection, establishment and development of gene sources for naturally-occurring resistance in soybean germplasm to exposure to the non-selective broad spectrum post-emergence herbicide glyphosate.

The identification of soybean germplasm within which naturally-occurring herbicide resistance genes reside involved the screening of thirty-four soybean lines obtained from publicly-available seed stocks. The initial step in the screening was to pre-soak individual batches of seeds representing the thirty-four test lines in a 2 percent aqueous solution of glyphosate at room temperature. The individual batches of seeds were immersed in this 2 percent solution for a period of six hours. Trials indicated that this amount of time commonly was necessary to allow the herbicide to penetrate the seed coat, and to affect the embryo and hence germination. This screening step was essential to determine how seeds responded to the herbicide. Twelve of the varieties were present as approximately 2,500 seeds. There were approximately 5,000 seeds of the remaining 22 varieties. Each variety was immersed in separate containers to assure variety identification and isolation. The varieties that were tested are identified in Table 1.

TABLE 1

Soybean varieties tested for the presence of glyphosate resistance.

| Variety | Source |
| --- | --- |
| 'Dwight' | University of Illinois - Dr. C. Nickel |
| 'Jack' | University of Illinois - Dr. C. Nickel |
| 'Macon' | University of Illinois - Dr. C. Nickel |
| 'Ina' | University of Illinois - Dr. C. Nickel |
| 'Rend' | University of Illinois - Dr. C. Nickel |
| 'Iroquois' | University of Illinois - Dr. C. Nickel |
| 'Pana' | University of Illinois - Dr. C. Nickel |
| 'Omaha' | University of Illinois - Dr. C. Nickel |
| 'Savoy' | University of Illinois - Dr. C. Nickel |
| 'Maverick' | University of Illinois - Dr. C. Nickel |
| 12 Non-pedigree lines Numbered 1–12 | Agri Pro Seed Ames, Iowa |
| 12 Non-pedigree lines Numbered 1–12 | Sommer Brothers Seed Perkin, Illinois |

After this initial pre-soak, each lot of seeds was labeled and was placed in a flat (36"×18"×9") containing a soil/peat mixture growth medium, with the mixture being 50 percent top soil (sandy loam) and 50 percent peat moss, that was provided at a depth of 9 inches. The 2 percent solution of glyphosate and water that previously had been used to soak the seeds was then poured over the seeds. A 2"-layer of the growth medium was spread over the seeds. Containers were placed in a greenhouse under ambient conditions and were watered to maintain the soil mix at or near field capacity.

Germination and emergence of any seedlings was then observed for the next three weeks. The majority of the herbicide-treated seeds failed to germinate. Of those that did germinate some died within a day or two and only five of the thirty-two tested lines produced any plants that survived the herbicide seed treatments and thus tolerated exposure to the glyphosate herbicide. These five lines were identified as lines that contained glyphosate resistance genes within their germplasm and were selected for further screening. Each of the five lines was obtained from the publicly released soybean varieties of the University of Illinois soybean breeding program. Of these five lines, the 'Dwight' and 'Jack' varieties were chosen for further screening using large quantities of seeds.

To maximize the yield of glyphosate resistant individual plants for analysis, and to maximize the likelihood of isolating an individual that had sufficient glyphosate resistance to act as a founder for a commercially viable glyphosate resistant soybean line and gene source, a direct screen for glyphosate resistance was initiated using the previously-identified 'Dwight' and 'Jack' soybean varieties. Without the prior screening via soaking in a herbicide and survivor identifications described above, this procedure would have been unduly burdensome.

Three hundred pounds, or approximately 840,000 seeds from each variety, ('Dwight' and 'Jack'), were planted in a five-acre block of land in Lubbock County, Tex. After emergence, and growth to the second tri-foliate leaf stage, glyphosate herbicide at the rate of one quart of herbicide per acre was applied to the field. An additional application at the same rate was applied approximately 10 days later. Thirty days after the second application of glyphosate, surviving plants were selected. Single-leaf samples from 346 surviving plants were collected and sent to Bio Diagnostics Inc., River Falls, Wis., for testing by PCR for the presence of the CaMV35S promoter, the only promoter used to date to control expression in commercial lines of soybean plants genetically engineered for glyphosate resistance, and the NOS marker gene, used in commercially available genetically engineered lines to generate kanamycin resistance for use as a selectable marker during soybean transformation. This analysis revealed that 178 plants tested free of both sequences indicating that these plants were not the result of an outcross to a commercially available transgenic glyphosate resistant soybean line.

The surviving plants, including those previously identified and tested, were exposed to a third application of glyphosate at the rate of one quart per acre in the field. In addition, as a result of delayed emergence, a large number of plants that were not exposed to the earlier treatments were exposed to the herbicide during this third treatment. As a result, an additional 161 new plants were sampled for testing for the presence of introduced genetic material, and of these 157 resulted in negative tests for both genes. All selected plants were further treated with herbicide, a 1 percent solution of glyphosate, by use of a hand sprayer in order to assure effective herbicide contact. All plants survived this additional herbicide treatment.

Throughout the PCR based testing of plant samples taken from survivors of the herbicide treatments random samples, along with positive controls, were chosen for duplicate testing in order to determine the reliability and consistency of the testing. As a result of this, 46 plants were tested multiple times and remained negative for the presence of both marker elements, the 35S promoter and the NOS sequence.

This screening of germplasm material from the 'Dwight' and 'Jack' soybean varieties, identified as germplasm containing natural glyphosate resistance genes by use of the seed treatment protocol, resulted in the isolation of 405 individual soybean plants that were capable of surviving exposure to glyphosate at a rate of one quart per acre or a 1 percent solution applied by a hand sprayer. Of these 405 individual soybean plants tested unequivocally 325 tested negative for the presence of either the 35S promoter or the NOS marker gene by virtue of the PCR based testing system of Bio Diagnostics Inc, River Falls, Wis. These plants were considered to contain within their genomes genes that when expressed delivered resistance to the of the glyphosate herbicide that was not the result of a genetic source currently present in commercially available soybean lines that was introduced into the germplasm of the two lines by plant transformation or other biotechnological means.

Of the 325 plants that tested negative for both the 35S promoter and the NOS marker gene only 230 had desirable growth characteristics and were kept for further testing. Each of these plants was grown to maturity and the seed produced by each plant was harvested and was kept separate. Approximately fifteen seeds from each plant were germinated in flats containing a mixture of 50 percent top soil (sandy loam) and 50 percent peat moss and the seedlings were allowed to grow to the first trifoliate stage. The seedlings were then exposed to a 2 percent solution of glyphosate applied by hand spraying. The seedlings were then evaluated approximately ten days following this treatment for presence of the 35S promoter and NOS marker gene, survival, growth characteristics, and plant morphology.

From this screening six plants exhibited the desired glyphosate resistance, absence of introduced gene sequences relating to commercial glyphosate resistance transgenes, appropriate growth characteristics, plant morphology, and level of seed production. As shown below five of these plants were derived from the 'Dwight' variety and one was derived from the 'Jack' variety. These plants and the results of the PCR based screening are presented in Table 2. Each line is capable of being selfed to produce a homozygous line that is suitable for conventional gene mapping and gene isolation protocols, know to those skilled in the art. Homozygous lines can be used to transfer genes responsible for the naturally-occurring herbicide resistance into superior soybean lines by traditional breeding strategies. Each line can be further tested for its performance in herbicide resistance trials. Each line has been renamed for ease of identification as shown in Table 3.

TABLE 2

Plant lines that express glyphosate resistance obtained from the present invention.

| Plant Designation | Original Variety | Glyphosate Resistance | PCR Test for 35S and NOS - Original Plant | PCR Test for 35S and NOS - Progeny Plants | Ratio Resistant/Sensitive (maximum 15 plants) |
|---|---|---|---|---|---|
| 159 | 'Jack' | + | Tested negative x 2 | 9 plants Tested - all negative | 13:0 |
| 221 | 'Dwight' | + | Tested negative x 2 | 3 plants Tested - all negative | 9:4 |
| 240 | 'Dwight' | + | Tested negative x 2 | 3 plants Tested - all negative | 11:2 |
| C-7 | 'Dwight' | + | Tested negative x 2 | 2 plants Tested - both negative | 2:1 |
| 324 | 'Dwight' | + | Tested negative x 2 | 3 plants Tested - all negative | 8:5 |
| L-14 | 'Dwight' | + | Tested negative x 2 | 9 plants Tested all negative | 11:3 |

TABLE 3

Re-designation key for plant lines described in Table 2.

| Experimental Plant | New Nomenclature |
|---|---|
| 159 | NatGen 1 |
| 221 | NatGen 2 |
| 240 | NatGen 3 |
| C-7 | NatGen 4 |
| 324 | NatGen 5 |
| L-14 | NatGen 6 |

On Oct. 24, 2002 a deposit of 2,500 seeds of soybean line NatGen 1 from which homozygous gene $NGR^{R1}NG^{R1}$ is obtainable was made under the terms of the Budapest Treaty at the American Type Culture Collection, 10801 University Boulevard, Manassas, Va. 20110-2209, U.S.A. and has received ATCC Accession No. PTA-4774.

On Apr. 29, 2004 a deposit of 2,500 seeds of soybean line NatGen 3 from which homozygous gene $NG^{R3}NG^{R3}$ is obtainable was made under the terms of the Budapest Treaty additionally was made at the same depository and has received ATCC Accession No. PTA-5937.

Seeds from each of the above-identified deposits will be irrevocably made available upon the grant of a patent that makes reference to these deposits. However, the availability of these seeds is not to be construed as a license to practice the claimed invention in contravention of rights granted under the authority of any government in accordance with its patent or breeder's rights laws.

Although the invention has been described with reference to preferred embodiments, it is understood that variations and modifications may be resorted to as will be apparent to those skilled in the art. Such variations and modifications are to be considered within the purview and scope of the claims appended hereto.

I claim:

1. A process for selecting a soybean plant which exhibits genetically-controlled herbicide resistance that is not attributable to genetic engineering comprising:
   (a) soaking mature soybean seeds in the absence of induced mutagenesis which are not genetically engineered for glyphosate herbicide resistance in a liquid comprising a glyphosate herbicide for a period of time sufficient for the herbicide to reach the embryos of the soybean seeds,
   (b) planting said soybean seeds following said soaking of step (a) in a growing medium and selecting at least one soybean plant that displays resistance to said glyphosate herbicide, and
   (c) confirming the resistance to said glyphosate herbicide in a soybean plant selected in step (b), which exhibits naturally-occurring genetically-controlled glyphosate herbicide resistance that is not attributable to a foreign gene for herbicide resistance introduced by genetic engineering.

2. The process according to claim 1 wherein said soaking of step (a) has a duration of at least 6 hours.

3. The process according to claim 1 wherein said glyphosate herbicide of step (a) is provided in an aqueous solution in a concentration of approximately 2 to 6 percent by weight.

4. A The process according to claim 1 wherein the soybean seeds of step (a) which are not genetically engineered for herbicide resistance are of the 'Dwight' variety.

5. The process according to claim 1 wherein the soybean seeds of step (a) which are not genetically engineered for herbicide resistance are of the 'Jack' variety.

6. The process according to claim 1 wherein in step (b) said liquid comprising a glyphosate herbicide of step (a) additionally is added to the growing medium of step (b).

7. The process according to claim 1 wherein the confirmation of step (c) is carried out on the basis of plant survival following contact with a glyphosate herbicide and the presence of a heritable gene for glyphosate herbicide resistance that is not attributable to a foreign gene for herbicide resistance introduced by genetic engineering.

8. The process according to claim 1 wherein step (b) is carried out by planting at least 5,000 soybean seeds following said soaking of step (a) in a growth medium, spraying the soybean plants that are produced with a glyphosate herbicide in a concentration sufficient to kill soybean plants and weeds that lack glyphosate herbicide resistance, and confirming the existence of a surviving soybean plant having genetically-controlled glyphosate herbicide resistance that is not attributable to a foreign gene for herbicide resistance introduced by genetic engineering.

9. The process according to claim 1 wherein said step (c) includes analyzing a portion of at least one soybean plant produced in step (b) to confirm the absence of a foreign gene for herbicide resistance introduced by genetic engineering.

10. A The process according to claim 9 wherein the portion of the soybean plant that is analyzed in step (c) is from a leaf.

11. A The process according to claim 9 wherein said analysis confirms the absence of a CaMV35S promoter, an ACTIN promoter, a NOS promoter, and a PCSLV promoter.

12. A The process according to claim 9 wherein said analysis confirms the absence of the Petunia EPSPS gene for glyphosate herbicide resistance.

13. A The process according to claim 9 wherein said analysis of confirms the absence of the CP4 gene for glyphosate herbicide resistance.

14. The process according to claim 2 wherein the soybean plant of step (c) is a progeny of the at least one soybean plant selected in step (b).

15. A process for selecting a soybean plant which exhibits genetically-controlled herbicide resistance that is not attributable to genetic engineering comprising:
   (a) soaking mature soybean seeds in the absence of induced mutagenesis which are not genetically engineered for glyphosate herbicide resistance selected from the 'Dwight' variety or the 'Jack' variety in a liquid comprising a glyphosate herbicide for a period of time sufficient for the herbicide to reach the embryos of the soybean seeds,
   (b) planting said soybean seeds following said soaking of step (a) in a growing medium and selecting at least one soybean plant produced upon the germination of said soybean seeds that displays genetically-controlled herbicide resistance following contact with said glyphosate herbicide that is not attributable to a foreign gene for herbicide resistance introduced by genetic engineering, and
   (c) optionally selecting a progeny plant from at least one selected soybean plant of step (b) that displays genetically-controlled glyphosate herbicide resistance.

* * * * *